US007053055B2

(12) United States Patent
Demuth et al.

(10) Patent No.: US 7,053,055 B2
(45) Date of Patent: May 30, 2006

(54) COMPOUNDS OF UNSTABLE DP IV-INHIBITORS

(75) Inventors: Hans-Ulrich Demuth, Halle/Saale (DE); Jorn Schmidt, Cologne (DE); Torsten Hoffmann, Halle/Saale (DE); Konrad Glund, Halle/Saale (DE)

(73) Assignee: Prosidion Ltd., Oxford (GB)

( * ) Notice: Subject to any disclaimer, the term of this patent is extended or adjusted under 35 U.S.C. 154(b) by 582 days.

(21) Appl. No.: 09/745,883

(22) Filed: Dec. 21, 2000

(65) Prior Publication Data

US 2001/0020006 A1 Sep. 6, 2001

Related U.S. Application Data

(63) Continuation of application No. PCT/EP99/04381, filed on Jun. 24, 1999.

(30) Foreign Application Priority Data

Jun. 24, 1998 (DE) .......................... 198 28 114

(51) Int. Cl.
*A61K 38/06* (2006.01)
*A61K 38/07* (2006.01)
*C07K 5/00* (2006.01)

(52) U.S. Cl. ............... 514/18; 514/19; 514/85; 514/89; 514/222.2; 435/219; 530/330; 530/331; 530/335; 530/338; 530/344

(58) Field of Classification Search ............ 514/18, 514/19, 85, 89, 222.2; 435/219; 530/330, 530/331, 335, 338, 344
See application file for complete search history.

(56) References Cited

U.S. PATENT DOCUMENTS

| 2,961,377 | A | 11/1960 | Shapiro et al. ............... 167/65 |
| 3,174,901 | A | 3/1965 | Sterne ......................... 167/65 |
| 3,879,541 | A | 4/1975 | Kabbe et al. ................ 424/326 |
| 3,960,949 | A | 6/1976 | Ahrens et al. ........... 260/564 B |
| 4,028,402 | A | 6/1977 | Fischer et al. ......... 260/501.14 |
| 4,935,493 | A | 6/1990 | Bachovchin et al. ....... 530/331 |
| 5,433,955 | A | 7/1995 | Bredehorst et al. ........ 424/94.3 |
| 5,462,928 | A | 10/1995 | Bachovchin et al. ......... 514/19 |
| 5,512,549 | A | 4/1996 | Chen et al. .................. 514/12 |
| 5,543,396 | A | 8/1996 | Powers et al. ................ 514/19 |
| 5,614,379 | A | 3/1997 | MacKellar ................ 435/68.1 |
| 5,624,894 | A | 4/1997 | Bodor ........................... 514/2 |
| 5,939,560 | A | 8/1999 | Jenkins et al. ............... 548/535 |
| 6,006,753 | A | 12/1999 | Efendic ....................... 128/898 |

FOREIGN PATENT DOCUMENTS

| DE | 25 42598 A1 | 10/1974 |
| DE | 25 42 598 A1 | 4/1976 |
| DE | 296 075 | 11/1991 |
| DE | 296 075 A5 | 11/1991 |
| DE | 19616486 | 10/1997 |
| EP | 0 658 568 A1 | 12/1994 |
| EP | 0 658 568 A1 | 6/1995 |
| EP | 0 708 179 A2 | 10/1995 |
| EP | 0 708 179 A2 | 4/1996 |
| EP | 0 995 440 A1 | 4/2000 |
| FR | 2085665 | 3/1971 |
| FR | 2 085 665 | 12/1971 |
| FR | 2696740 | 10/1992 |
| FR | 2 696 740 A1 | 4/1994 |
| JP | 04-288098 | 10/1992 |
| JP | 4334357 | 11/1992 |
| JP | 4334357 A2 | 11/1992 |
| WO | WO 91/11457 | 8/1991 |
| WO | WO 91/16339 | 10/1991 |
| WO | WO 91/17767 | 11/1991 |
| WO | 9308259 A2 | 4/1993 |
| WO | 9511689 | 5/1995 |
| WO | WO 95/15309 | 6/1995 |
| WO | WO 95/29691 | 11/1995 |
| WO | WO 97/40832 | 11/1997 |
| WO | 9745117 | 12/1997 |
| WO | WO 98/19998 | 5/1998 |
| WO | WO 98/22494 | 5/1998 |
| WO | WO 00/01849 | 1/2000 |
| WO | WO 00/53171 | 9/2000 |
| WO | WO 01/62266 A2 | 8/2001 |

OTHER PUBLICATIONS

Stryer (1975) Biochemistry, pp. 451–452 (W.H. Freeman and Company, San Francisco).*

Wakselman, M., Nguyen, C., Mazaleyrat, J.–P., Callebaut, C., Krust, B., Hovanessian, A.G., Inhibition of HIV–1 infection of CD 26+ but not CD26–cells by a potent cyclopeptidic inhibitor of the DPP IV activity of CD 26. Abstract P 44 of the 24th European Peptide Symposium 1996.

Willms, B. et al., Gastric Emptying, Glucose Response, and Insulin Secretion after a Liquid Test Meal: Effects of Exogenous Glucagon–Like Peptide–1 (GLP–1)–(7–36) Amide in Type 2 (Noninsulin–Dependent) Diabetic Patients. *JCEM* 81:327–332 (1996).

Campbell, I.W. New Antidiabetic Drugs, ed. C.J. Bailey & P.R. Flatt, Smith–Gordon, "Sulphonylureas and metformin: efficacy and inadequacy". 3:33–51 (1990).

The Merck Index, 11th Edition, An Encyclopedia of Chemicals, Drugs, and Biologicals, 1996, p. 934.

Martindale The Extra Pharmacopoeia, 30th Edition, London Pharmaceutical Press, 1993, p. 1619.

(Continued)

*Primary Examiner*—Jon Weber
*Assistant Examiner*—Chih-Min Kam
(74) *Attorney, Agent, or Firm*—Shu M. Lee (57) ABSTRACT

Novel compounds of unstable inhibitors of the serine peptidase dipeptidyl peptidase IV, are used in the treatment of various disorders, especially of metabolic disorders. The compounds can be used in the treatment of impaired glucose tolerance, glucosuria, hyperlipidaemia, metabolic acidoses, diabetes mellitus, diabetic neuropathy and nephropathy.

16 Claims, 8 Drawing Sheets

OTHER PUBLICATIONS

Chemical Abstracts, vol. 115, No. 15, Oct. 14, 1991 Columbus, Ohio, US; abstract No. 149947q, Schoen Ekkehard et al: "Dipeptidyl peptidase IV in the immune system. Effects of specific enzyme inhibitors on activity of dipeptidyl peptidase IV and proliferation of human lymphocytes".

Chemical Abstracts, vol. 126, No. 2, Jan. 13, 1997 Columbus, Ohio, US; abstract No. 16161j, Stoeckel A. et al: "Competitive inhibition of proline specific enzymes by amino acid thioxopyrrolidides and thiazolidides".

Chemical Abstracts, vol. 118, No. 25, Jun. 21, 1993 Columbus, Ohio, US; abstract No. 255342k, Hosoda, et al, "Preparation of N–(heterocyclic Carbonyl) Amino Acids and Analogs as Prolyl Endopeptidase Inhibitors", Nov. 1992.

Arai et al: "Synthesis of prolyl endopeptidase inhibitors and evaluation of their structure–activity relationships : invitro inhibition of prolyl endopeptidase from Canine Brain" Chemical and Pharmaceutical Bulletin., Bd. 41, No. 9, pp. 1583–1588.

Amasheh, S., et al., "Electrophysiological analysis of the function of the mammalian renal peptide transporter expressed in Xenopus Laevis oocytes". J. Physiol. 504, 169–174 (1997).

Hoffmann et al., *Journal of Chromatography A*, "Inhibition of dipeptidyl peptidase IV (DP IV) by anti–DP IV antibodies and non–substrate X–X–Pro– oligopeptides ascertained by capillary elctrophoresis", 1995, 716:355–362.

Hendrick et al., *Metabolism—Clinical and Experimental*, "Glucagon–like Peptide–I–(7–37) Suppresses Hyperglycemia in Rats", Jan. 1993, 42(1): 1–6.

Nauck et al., *Diabetologia*, "Normalization of fasting hyperglycaemia by exogenous glucagon–like peptide 1 (7–36 amide) in Type 2 (non–insulin–dependent) diabetic patients", 1993, 36: 741–744.

Gutniak et al., *Diabetes Care*, "Subcutaneous Injection of the Incretin Hormone Glucagon–Like Peptide 1 Abolishes Postprandial Glycemia in NIDDM", Sep. 1994, 17(9): 1039–1044.

Deacon et al., *Journal of Clinical Endocrinology and Metabolism*, "Degradation of Glucagon–Like Peptide–1 by Human Plasma in Vitro Yields and N–Terminally Truncated Peptide That Is a Major Endogenous Metabolite in Vivo", 1995, 80(3):952–957.

Pauly et al., *Metabolism*, "Improved Glucose Tolerance in Rats Treated with the Dipeptidyl Peptidase IV (CD26) Inhibitor Ile–Thiazolidide", 1999, 48(3): 385–389.

Thorens et al., *Diabetes*, "Glucagon–Like Pepetide–I and the Control of Insulin Secretion in the Normal State and in NIDDM", 1993, 42:1219–1225.

J. Lin et al.: "Inhibition of dipeptidyl peptidase IV by fluoroolefin–containing n–peptidyl–0–hydroxylamine peptidomimetics" Proceedings of the National Academy of Sciences of USA, Bd. 95, Nov. 1998, Seiten 14020–14024, XP002117450 Washington US Seite 14023, rechte Spalte, Absatz 3—Seite 14024, linke Spalte, Absatz 1.

Korom, S., Demeester, I., Stadlbauer, T.H.W., Chandraker, A., Schaub, M, Sayegh, M.H., Belyaev, A., Haemers, A., Scharpe, S., Kupiec–Weglinski, J.W., Inhibition of CD26/dipeptidyl peptidase IV activity in vivo prolongs cardiac allograft survival in rat recipients, Transplantation 63, 1495 (1997).

Tanka, S., Murakmi, T., Horikawa, H., Sugiura, M., Kawashima, K., Sugita, T., Suppression of arthritis by the inhibitors of dipeptidyl peptidase IV. Int. J. Immunopharmacol. 19, 15 (1997).

Mentlein, R., Dahms, P. Grandt, D., Kruger, R., proteolytic processing of neuropeptide Y and peptide YY by dipeptidyl peptidase IV. Regul. Pept. 49, 133 (1993).

Wetzl, W., Wagner, T., Vogel, D., Demuth, H.–U., Balschun, D., Effects of the CLIP fragment ACTH 20–24 on the duration of REM sleep episodes. Neuropeptides, 31, 41 (1997).

The Merck Index, 12$^{th}$ Edition, *An Encyclopedia of Chemicals, Drugs*, and Biologicals, 1996, p. 1014.

*Martindale The Extra Pharmacopoeia*, 30$^{th}$ Edition, London Pharmaceutical Press, 1993, p. 36.

Durinx, C.; et al.; et al.; "Reference Values for Plasma Dipepidyl–Pepidase IV activity and their Association with Other Laboratory Parameters". *Clin Chem Lab Med 2001*, Feb.; 39 (2) :155–9, 1 page.

Gossrau, R.; "Cytochemistry of Membrane Proteases", *Histochem J*, Jul. 1985; 17 (7) :737–71, 1 page.

Hahn. T.; et al.; "Enzyme Histochemical Evidence for the Presence of Potential Blood Pressure Regulating Proteases in Cultured Villous Explants from Human First Trimester Pacentae". *Acta Histochem* Dec. 1993, 95 (2) :185–92, 1 page.

Heymann, E. et al., "Has Dipeptidyl Peptidase IV an Effect on Blood Pressure and Coagulation." *Klin Wochenschr*, Jan. 1984, 2;62 (1) :2–10, 1 page.

Magyar, C.E. et al., "Proximal Tubule Na Transporter Responses are the same during Acute and Chronic Hypertension." *Am J. Physiol Renal Physiol*, Aug. 2000; 279 (2) :F358–69, 1 page.

Papies, B. et al., "Isoenzyme (Lactate Dehydrogenase, Aspartate Aminotransferase) and Dipeptidyl Peptidase IV Activity Changes in Blood Plasma Likely Indicative of Organ Involvement due to Arterial Hypertension." *Cor Vasa*, 1991; 33 (3) :218–26, 1 page.

Qureshi. N.U.; et al., "Endogenous Neuropeptide Y Mediates Vasoconstriction during Endotoxic and Hemorrhagic Shock". *regul Pept*, Sep. 25, 1998; 75–76:215–20, 1 page.

Index Nominum, *International Drug Directory 1992/1993*, Medpharm Scientific Publishers, pp. 728–729.

The Merck Index, *An Encylopedia of Chemicals and Drugs*, 9$^{th}$ Edition, Merck & Co., Inc., 1976, p. 773.

C.J. Bailey et al., New Antidiabetic Drugs, Smith–Gordon Nishimura, 1990, p. 36.

C.B. Welch, *Medical Management of Non–Insulin–Dependent (Type II) Diabetes*, 3$^{rd}$ edition, American Diabetes Association, "Diagnosis and Classification" p. 3, 1994, Pharmacologic Intervention (2 pages).

Mannucci et al., *Diabetes Care*, "Effect of Metformin on Glucagon–Like Peptide 1 (GLP–1) and Leptin Levels in Obese Nondiabetic Subjects", 24(3): 489–494, Mar. 2001.

Stryer, *Biochemistry 3$^{rd}$ $^{Ed}$*., "Protein Conformation, Dynamics, and Function", 1988, p 191–193.

Pauly et al., *Regulatory Peptides*, "Abstracts Issue: Abstracts from the 11$^{th}$ International Symposium on Regulatory Peptides", Jul. 15, 1996, 64(1–3): 148 plus cover.

Gutniak et al., *New England Journal of Medicine*, "Antidiabetogenic Effect of Glucagon–like peptide–1 (7–36) Amide in Normal Subjects and Patients With Diabetes Mellitus", 1992, 326: 1316–1322.

H.A. Smith et al., *Veterinary Pathology* (fourth edition), "Diseases and Disorders of Metabolism: Deficiency Diseases", (1972), p 1018–1020.

G.G. Duncan, *Diseases of Metabolism (Asian edition)*, "Diabetes Mellitus", (1966), p 951–957.

T.J. Kieffer et al., "Degradation of Glucose–Dependent Insulinotropic Polypeptide and Truncated Glucagon–Like Peptide 1 In Vitro and In Vivo by DP IV", *Endocrinology*, vol. 136(8), (1995), p 3585–3596.

C.F. Deacon et al., *Diabetes*, "Both Subcutaneously and Intravenously Administered Glucagon–Like Peptide I Are Rapidly Degraded from the $NH_2$–Terminus in Type II Diabetic Patients and in Healthy Subjects", Sep. 1995, 44: 1126–1131.

*Vidal*, (1993), $69^{th}$ Edition, p. 612–613.

*Goodman & Gilman's The Pharmacological Basis of Therapeutics*, Ninth Edition, (1996), p. 1510.

Nathan et al., *Diabetes Care*, "Insulintropic Action of Glucagonlike Peptide–1–(7–37) in Diabetic and Nondiabetic Subjects", Feb. 1992, 15(2): 270–275.

Frohman et al., *Journal of Clin. Invest.*, "Rapid Enzymatic Degradation of Growth Hormone–releasing Hormone by Plasma in Vitro and in Vivo to a Biologically Inactive Product Cleaved at the $NH_2$ Terminus", vol. 78, Oct. 1986, p 906–913.

Snow et al., *Advances In Medicinal Chemistry*, "Boronic Acid Inhibitors of Dipeptidyl Peptidase IV: A New Class of Immunosuppressive Agents", vol. 3, (1995), p 149–177.

Ashworth et al., *Bioorg. Med. Chem. Lett.*, "2–Cyanopyrrolidides as Potent, Stable Inhibitors of Dipeptidyl Peptidase IV", (1996), 6(10): 1163–1166.

Endroczi et al., *Acta Physiol. Hung.*, "Dipeptidyl peptidase IV (DP IV) and Superoxide Dismutase Activity in Thymus–Derived Lymphocytes: Effects of Inhibitory Peptides and $Zn^{2+}$ in Vitro", (1990), 75(1): 35–44.

Lee, H.S. et al., "Cathepsin B Inhibitory Peptides Derived from β–Casein," *Peptides* 21 (2000) 807–809.

Edwards, J.V. et al., *J. Peptide Res.*, "Synthesis and Activity of $NH_2$ –and COOH–Terminal Elastase Recognition Sequences on Cotton," (1999), 54: 536–543.

Campbell, I.W., Sulphonylureas and metfromin: efficacy and inadequacy. 3:33–51 (1990).

Mercla Index, $11^{th}$ Edition, p. 934.

Martindale the Extra, Pharmacopoeia, p. 1619.

Arai, H. et al: "Synthesis of prolyl endopeptidase inhibitors and evaluation of their structure–actvity relationships : in vitro inhibition of prolyl endopeptidase" Chemical and Pharmaceutical Bulletin., Bd. 41, Nr. 9, 1993 pp. 1583–1588.

Amasheh, S. et al., Electrophysiological analysis of the funtion of the mammalian renal peptide transporter expressed in Xenopus Laevis oocytes. J. Physiol. 504, 169–174 (1997).

Chemical Abstracts, vol. 115, No. 15, Oct. 14, 1991 Columbus, Ohio, US; abstract No. 149947q, Schoen Ekkehard et al: "Dipeptidyl peptidase IV in immune system.Effects of specific enzyme inhibitors on activity of dipeptidyl peptidase IV and proliferation of human lymphocytes" Seite 37; XP002114197 Zusammenfassung & Biol. Chem. Hoppe–Seyler, Bd. 372, Nr. 5, 1991, Seiten 305–311.

Chemical Abstracts, vol. 126, No. 2, Jan. 13, 1997 Columbus, Ohio, US; abstract No. 16161j, Stoeckel A. et al: "Competitive inhibition of proline specific enzymes by amino and acid thioxopyrrolidides and thiazolidides" Seite 241; XP002114198 Zusammenfassung & Pept: Chem., Struct.Biol., Proc.Am.Pept.Symp., Nr. 14, 1995, Seiten 709–710.

Chemical Abstracts, vol. 118, No. 25, Jun. 21, 1993 Columbus, Ohio, US; abstract No. 255342k, Seite 933; XP002114199 Zusammenfassung & JP 04 334357 A (Fujerebio Inc) Nov. 20, 1992.

Thorens, B et al., Glucagon–Like Peptide–I and the Control of Insulin Secretion in the Normal State and in NIDDM. *Diabetes* 42:1219–1225 (1993).

Orskov C. et al., Proglucagon Products in Plasma of Non-insulin–dependent Diabetics and Nondiabetic Controls in the Fasting State and After Oral Glucose and Intravenous Argine. *J. Clin. Invest.* 87:415–423 (1991).

Pauly, R. et al., Improved Glucose Tolerance in Rats Treated with the Dipeptidyl Peptidase IV (CD26) Inhibitor ILE–Thiazolidide. *Metabolism* 48:385–389 (1999).

Winslow, R., Novartis Drug Alters Picture for Diabetes. *Wall Street Journal*, Wed. Dec. 27, 2000, p. B2.

Hendrick, G.K. et al., Glucagon–Like Peptide–I–(7–37) Suppresses Hyperglycemia in Rats. *Metabolism* vol. 42, No. 1, p. 1–6 (Jan. 1993).

Deacon, C. et al., Degradation of Glucagon–Like Peptide–1 by Huamn Plasma in yeilds Vitro an N–Terminally Truncated Peptide that is a Major Endogenous Metabolite in Vivo. *JCEM* 80:952–957, (Apr. 25, 1995).

Hoffman, T. et al., Inhibition of Dipeptidyl Peptidase IV (DPIV) by anti–DP IV antibodies and non–substrate X–X–Pro– Oligopeptides Ascertained by Capillary Electrophoresis. *Journal of Chromatography A, 716* 355–362 (1995).

Nauck, M.A. et al., Normalization of Fasting Hyperglycaemia by Exogenous Glucagon–Like Peptide 1 (7–36 Amide) in Type 2 (Non–insulin–dependent) Diabetic Patients. *Diabetologia* 36:741–744 (1993).

Gutniak, M. K. et al., Subcutaneous Injection of the Incretin Hormone Glucagon–Like Peptide 1 Abolishes Postprandial Glycemia in NIDDM. *Diabetes Care* 17:1039–1044, (Sep. 1994).

* cited by examiner

Figure 1: Structural formula of the product of the intramolecular cyclisation of H-Phe-Pro-pyridinium methyl ketone. The characteristic chemical displacements (in ppm) determined by means of $^{13}$C NMR and $^{1}$H NMR are assigned to the corresponding atoms.

Figure 2: MALDI-TOF mass spectra of the cyclisation of H-Phe-Pro-pyridinium methyl ketone in an aqueous buffer solution pH = 7.6, recorded according to the incubation period.

Figure 3: MALDI-TOF mass spectra of the cyclisation of H-Val-Pro-pyridinium methyl ketone in an aqueous buffer solution pH = 7.6, recorded according to the incubation period.

Figure 4: UV spectra of an aqueous solution of H-Phe-Pro-pyridinium methyl ketone incubated in 0.1M HEPES buffer, pH = 7.6, at 30°C. The cyclisation reaction was monitored over a period of 40 minutes.

Figure 5: Progress curves of the DP IV-catalysed hydrolysis of the substrate H-Gly-Pro-pNA in the presence of $2.8 \times 10^{-3}$M H-Val-Pro-pyridinium methyl ketone, 0.06 µg/ml of DP IV, $4 \times 10^{-4}$M H-Gly-Pro-pNA in the batch, 0.1M HEPES buffer, pH = 7.6, 30°C.

Figure 6: Progress curves of the DP IV-catalysed hydrolysis of H-Gly-Pro-pNA in the presence of $2.1 \times 10^{-4}$ M H-Phe-Pro-pyridinium methyl ketone, 0.06 µg/ml of DP IV, $1.0 \times 10^{-3}$ mol/litre of H-Gly-Pro-pNA in the batch, 0.1M HEPES buffer, pH = 7.6, 30°C.

Figure 7: MALDI-TOF mass spectrum of the incubation batch of the DP IV-catalysed hydrolysis of H-Gly-Pro-pNA in the presence of $2.6 \times 10^{-5}$ mol/litre of H-Gly-Pro-Val-Pro-pyridinium methyl ketone, 0.06 µg/ml of DP IV, $2.0 \times 10^{-4}$ mol/litre of H-Gly-Pro-pNA, 0.1M HEPES buffer, pH = 7.6, 30°C. Recorded after an incubation period of 60 minutes.

Figure 8: Progress curves of the DP IV-catalysed hydrolysis of H-Gly-Pro-pNA in the presence of $2.6 \times 10^{-5}$ mol/litre of H-Gly-Pro-Val-Pro-pyridinium methyl ketone, 0.06 µg/ml of DP IV, $2.0 \times 10^{-4}$ mol/litre of H-Gly-Pro-pNA in the batch, 0.1M HEPES buffer, pH = 7.6, 30°C.

COMPOUNDS OF UNSTABLE DP IV-INHIBITORS

CROSS REFERENCE TO OTHER APPLICATIONS

This application is a Continuation of PCT/EP99/04381, filed Jun. 24, 1999, which claims the priority of German Application No. DE 19828114.5, filed Jun. 24, 1998.

BACKGROUND OF THE INVENTION

Aminoacyl thiazolidides, aminoacyl pyrrolidides, N-dipeptididyl, O-acyl hydroxylamines and other compounds are known to act as inhibitors of the serum enzyme dipeptidyl peptidase IV (DP IV) and of analogous enzymes (see DEMUTH, H.-U., J. Enzyme Inhibition 3, 249 (1990); DEMUTH, H.-U., HEINS, J., in *Dipeptidyl Peptidase IV* (B. Fleischer, Ed.) R.G. Landes, Biomedical Publishers, Georgetown, 1995, 1–37).

It has been found that the T-cell-mediated immune response, for example in the case of transplantations, is influenced by means of stable inhibitors of dipeptidyl peptidase IV, (see KOROM, S., DEMEESTER, I., STADLBAUER, T.H.W., CHANDRAKER, A., SCHAUB, M., SAYEGH, M.H., BELYAEV, A., HAEMBRS, A., SCHARPE, S., KUPEC-WEGLINSKI, J.W., Inhibition of CD26/dipeptidyl peptidase IV activity in vivo prolongs cardiac allograft survival in rat recipients, Transplantation 63, 1495 (1997)). Rheumatoid arthritis can also be suppressed (see TANAKA, S., MURAKAMI, T., HORIKAWA, H., SUGIURA, M., KAWASHIMA, K., SUGITA, T., Suppression of arthritis by the inhibitors of dipeptidyl peptidase IV. Int. J. Immunopharmacol. 19, 15 (1997)).

It has also been found that, because of the associated temporary reduction in enzyme activity, administering stable inhibitors (effectors) of DP IV or of DP IV-analogous enzyme activity in the blood of a mammal causes reduced breakdown of the endogenous (or additionally exogenously administered) insulinotropic peptides gastric inhibitory polypeptides 1–42 ($GIP_{1-42}$) and glucagon-like peptide amides-1 7–36 ($GLP-1_{7-36}$) (or $GLP-1_{7-37}$ or analogues thereof) by DP IV and DP IV-like enzymes and, accordingly, the drop in concentration of those peptide hormones or analogues thereof is reduced or delayed. The greater stability of the (endogenously present or exogenously introduced) incretins or analogues thereof, brought about by the action of the DP IV-effectors, which increases their availability for insulinotropic stimulation of the incretin receptors of the Langerhans cells in the pancreas, inter alia alters the effectiveness of the body's own insulin, resulting in stimulation of carbohydrate metabolism in the organism treated. As a result, the blood sugar level in the serum of the organism treated falls below the glucose concentration characteristic of hyperglycaemia. Consequently, by means of DP IV-inhibitors it is possible to prevent or alleviate metabolic anomalies, such as excess weight, glucosuria, hyperlipidaemia, and possible serious metabolic acidoses and diabetes mellitus, which are the result of prolonged elevated glucose concentrations in the blood (see DE 196 16 486).

By means of DP IV-inhibitors it is also possible, experimentally, to prevent the penetration of CD 26 (DP IV) positive cells by HIV (see WAKSELMAN, M., NGUYEN, C., MAZALEYRAT, J.-P., CALLEBAUT, C., KRUST, B., HOVANESSIAN, A.G., Inhibition of HIV-1 infection of CD 26+ but not CD26-cells by a potent cyclopeptidic inhibitor of the DPP IV activity of CD 26. Abstract P 44 of the 24th European Peptide Symposium 1996).

It has also been found that DP IV can modulate the activity of neuroactive peptides, such as neuropeptide Y and CLIP (see MENTLEIN, R., DAHMS, P., GRANDT, D., KRUGER, R., Proteolytic processing of neuropeptide Y and peptide YY by dipeptidyl peptidase IV. Regul. Pept. 49, 133 (1993); WETZL, W., WAGNER, T., VOGEL, D., DEMUTH, H.-U., BALSCHUN, D., Effects of the CLIP fragment ACTH 20–24 on the duration of REM sleep episodes. Neuropeptides, 31, 41 (1997)).

These varied actions of DP IV-inhibitors suggest that, when used in the case of a specific pathophysiological condition of a tissue, their actions can have an effect on other normal physiological states, for example in other organs. Those effects can have both positive and negative consequences for the target organism.

The problem of the present invention is accordingly to provide effectors of DP IV that have a high bioavailability of DP IV-inhibitors and a precisely defined duration of action in specific target tissues or target organs.

It was especially a problem of the present invention to provide inhibitors of DP IV that have a precisely defined short duration of action combined with high bio-availability.

SUMMARY OF THE INVENTION

The problems of the prior art are solved by the provision of compounds of unstable inhibitors of dipeptidyl peptidase IV (DP IV), which compounds have the general formula A—B—C, wherein A is an amino acid, B is a chemical bond between A and C or is an amino acid, and C is an unstable inhibitor of DP IV.

When B represents a bond, it is especially a peptide bond; when B is an amino acid, it is preferably linked to A and C by way of peptide bonds.

The present invention accordingly relates to novel compounds of unstable inhibitors of the serine peptidase dipeptidyl peptidase IV, which compounds can be used in the treatment of various disorders, especially of metabolic disorders associated with diabetes mellitus.

Surprisingly such masked inhibitors are additionally considerably more effective than non-masked inhibitors: if identical amounts of non-masked DP IV-inhibitors and of compounds according to the invention are used, the compounds according to the invention produce a marked improvement in glucose tolerance in Wistar rats.

A further advantage of the compounds according to the invention lies in the fact that the onset of action and also the duration of action of the DP IV-inhibitors can be temporally controlled by suitable selection of the groups A—B. In particular, the release of the groups A—B from the compounds according to the invention depends upon the nature of the amino acid radical of A: in respect of the definition of group A, the following sequence has been found in particular for the rate at which the radicals A—B are released from the compounds A—B—C by DP IV: Ile<Val<Phe<Pro<Ala<Gly. The rate constants of the corresponding DP IV-catalysed release are from $1\ s^{-1}$ to $100\ s^{+1}$. A means is thus available for releasing the DP IV-inhibitors in a precisely temporally defined manner: if the enzymes are to act immediately, for example upon intake of glucose-rich nutrient, a compound A—B—C will be selected that has, for example, the amino acid Gly as the A group; if the action of the inhibitor is to be delayed then the amino acid Ile, for example, can be selected as group A.

By means of the compounds according to the invention, it is thus possible for the DP IV-inhibitors to be transported through the mucosa of the small intestine especially virtually without delay, for example virtually simultaneously with nutrient intake.

Moreover, the site at which the DP IV-inhibitors are released and at which they act can also be controlled by the nature of the radicals A—B:

Various other amino peptidases, such as, for example, pyroglutamyl aminopeptidase and prolyl aminopeptidase, are present in the blood of mammals in addition to dipeptidyl peptidase IV. By suitable selection of the radicals A—B, it is possible according to the invention to determine the aminopeptidase by which the DP IV-inhibitor is to be released and so to determine where the action of the inhibitor is to occur. The compounds according to the invention or corresponding pharmaceutical compositions can thus also be used in cell-, tissue- or organ-specific inhibition of DP IV. The groups A—B can also be so selected that only those enzymes that are present only vascularly and that release the inhibitors at a sufficiently fast rate are targeted.

To summarize, it may be stated that by means of the compounds of unstable DP IV-inhibitors according to the invention, it is possible, in a completely surprising manner:

1. to achieve increased action of the inhibitors;

2. for the inhibitors to be released according to patients' needs;

3. for the inhibitors to be released from the compounds in a temporally controlled manner;

4. for the site at which the inhibitors are released from the compounds to be controlled;

5. for a reservoir of DP IV-inhibitors to be provided; and 6. for the duration of action or the end of action of the initiators to be precisely defined from the time of their unmasking.

According to the invention there are also provided pharmaceutical compositions especially for oral administration, characterized in that they comprise at least one compound according to the invention optionally in combination with customary carriers or excipients.

The compounds according to the invention or pharmaceutical compositions comprising them can be used in the treatment or prophylaxis of disorders in mammals that can be treated by modulating the DP IV activity of a mammal, such as, for example, metabolic disorders in humans.

In particular they can be used in the treatment of impaired glucose tolerance, glucosuria, hyperlipidaemia, metabolic acidoses, diabetes mellitus, diabetic neuropathy and nephropathy and sequelae of diabetes mellitus in mammals.

Because of the preferably short duration of action of the unstable inhibitors according to the invention, it is especially possible to minimize or prevent an influence upon processes in the human or animal body that would require long-term inhibition of DP IV.

BRIEF DESCRIPTION OF THE DRAWINGS

The foregoing and other features and advantages of the present invention will be more fully understood from the following detailed description of illustrative embodiments, taken in conjunction with the accompanying drawings in which.

DETAILED DESCRIPTION OF THE INVENTION

According to the invention, those compounds can be used as inhibitors of DP IV, it being possible for the site of their action, the time of onset of their action and the duration of action to be defined precisely:

Upon administration, the compounds are cleaved, for example by suitable enzymes, and the unstable "C" inhibitors are thus released by removal of the groups A—B. The inhibitors are released both by chemical and enzymatic mechanisms. For example, esterases, proteases and peptidases serve to release the active ingredient from compounds according to the invention. Such esterases, proteases, etc., are disclosed, for example, in WO 97/45117, US 5433955, US 5614379 and US 5624894.

The released unstable inhibitors can then interact with the DP IV already present and inhibit it. As a direct result, for example, the above-mentioned insulinotropic peptides are broken down to a lesser degree and the effectiveness of insulin is thereby increased.

The administration of unstable inhibitors of DP IV per se has proved disadvantageous for inhibiting DP IV since they are broken down very rapidly in vivo and thus uniform distribution of the inhibitors, especially in the human body, is impossible. In particular, upon oral administration such inhibitors are so unstable that they have virtually no activity at all. Accordingly, stable inhibitors have hitherto been used especially in the treatment of diabetes mellitus.

Surprisingly it has now been found that unstable "C" inhibitors can be stabilized sufficiently by masking them as groups of the formula A—B—C.

That stabilization is also surprising insofar as a compound of formula A—B—C that has a carbonylmethyl pyridinium group is positively charged at the pyridinium nitrogen atom. As a result, electron-attraction is exerted by the methylene group upon the group that, after removal of the A—B radical, constitutes the active nucleophilic reaction centre of the inhibitor. On the basis of the resulting activation of the reaction centre, it would have been expected that its nucleophilic tendency would have been increased to such an extent that nucleophiles would "dock" non-specifically at the compound A—B—C and the inhibitor would be inactivated. Surprisingly it has been found, however, that such inactivation of the inhibitors does not occur.

In order to intervene by means of DP IV-inhibitors in physiological control circuits that require only a short-term effect upon the target enzyme DP IV, according to the invention there are provided, for example, inhibitors as component C that have only a short duration of action and that after a definable half-life become chemical compounds that have no inhibitory activity.

For example, to strengthen the incretin effect in diabetes mellitus a duration of action of the inhibitors of a few minutes is sufficient whilst, for example, the suppression of the DP IV-mediated immune response in the case of transplantations requires long-term action by the inhibitors.

After being released, the unstable inhibitors according to the invention cyclise, for example, into a piperazine derivative and are thus inactivated. That reaction occurs spontaneously and is attributable to the nucleophilic action of the N-terminal amino nitrogen on the C-terminal carbonyl function of the dipeptide derivative and is facilitated by cis/trans isomerisation around the amino acid/imide bond, which isomerisation is facilitated especially in proline-containing peptides.

Moreover, that decomposition process does not begin until the compound has reached the desired target compartment, for example the blood circulation, and has begun the desired activity.

Those properties of the inhibitors according to the invention can be used according to the invention to design different DP IV-inhibitors in order to trigger the desired temporally defined deactivation of the DP IV-inhibitor by intramolecular cyclisation after it has been released.

In particular, according to the invention preference is given to compounds in which C is a dipeptide derivative having an active carbonyl group at the C-terminus. Preferably C is a dipeptidyl chloroalkyl ketone, dipeptidyl boronic acid or dipeptidyl cyanide compound or a dipeptidyl pyridinium methyl keto compound. Such inhibitors have proved to be especially effective unstable DP IV-inhibitors. There may be mentioned as examples of the dipeptide group, for example Ile-Thia, Ile-Pyr, Val-Thia and Val-Pyr. According to the invention, the inhibitors (component C) may also be present in salt form, with preference being given to organic salts, such as acetates, succinates, tartrates or fumarates, or to inorganic acid radicals, such as phosphates or sulphates. Special preference is given to fumarates.

According to a preferred embodiment of the present invention, compounds are used in which B is proline, hydroxyproline, thiazolidinecarboxylic acid, dehydroproline, pipecolic acid, 2- or 3-azetidinecarboxylic acid, or 2-aziridinecarboxylic acid, with proline and hydroxyproline being especially preferred.

In particular, the compounds according to the invention also have the advantage that the inhibitors of DP IV are released according to individual patients' needs:

When a compound according to the invention interacts with a DP IV molecule, it is cleaved by the enzyme into the groups A—B and the inhibitor C. The inhibitor C will inhibit the DP IV molecule so that it cannot cleave any further compounds. If further DP IV molecules are present, the compounds will continue to be cleaved (if a sufficient amount of corresponding compounds has been administered) until the last DP IV molecule has been inhibited. The remaining compounds are not broken down and thus constitute an inhibitor reservoir until the concentration of DP IV molecules rises again or inhibitor molecules are displaced by the DP IV or inhibitor molecules are eliminated or inactivated, and the compounds according to the invention are then cleaved again, thus releasing inhibitors.

The invention also has the further advantage that each organism will release the exact amount of inhibitor that is necessary to inhibit the amount of DP IV present, which is different in individual cases. If, for example, a patient has a high concentration of DP IV then a large amount of inhibitor will be released; if there is only a slightly elevated concentration of DP IV, only a small amount of inhibitor will be released.

In particular, special preference is given to compounds in which A—B is a dipeptide of the formula Ile-Pro or Gly-Pro.

Embodiments

Synthesis of unstable DP IV-inhibitors C and compounds of unstable DP IV-inhibitors according to the invention (A—B—C)

The preparation of unstable DP IV-inhibitors C (corresponding to the general formula A—B—C) is shown in Examples 1.1 and 1.2. The synthesis of a compound of unstable DP IV-inhibitors according to the invention is shown in Example 1.3. The starting materials, the corresponding peptidyl chloromethyl ketones in each case, were prepared according to known processes (WEINSTEIN, B., Chemistry and Biochemistry of Amino Acids, Peptides, and Proteins, Marcel Dekker, New' York, Basle, 1977). The pyridinium methyl ketones prepared by way of example under 1.1 and 1.2, which are N-terminal-protected dipeptide derivatives, are extremely stable and can be characterized completely. At normal air humidity, the N-terminal deblocked dipeptide derivatives begin the intramolecular decomposition process immediately after being deblocked, so that it is not possible to determine a melting point. The products are characterized by means of HPLC and mass spectrometry.

1.1 Synthesis of H-Val-Pro-CH$_2$—(N$^+$C$_5$H$_5$)/Cl a) Z-Val-Pro-CH$_2$—(N$^+$C$_5$H$_5$)/Cl

Structural formula:

Preparation: 10 mmol of Z-Val-Pro-chloromethyl ketone are dissolved in pyridine and stirred at 25° C. for 5 days. The excess pyridine is distilled off at 2 mbar vacuum. The Z-Val-Pro-pyridinium methylketone is subjected to HPLC purification. The compound is an oil.

Empirical formula: $C_{24}H_{30}N_3O_4Cl$
Molecular weight: 459.97 Da
Yield: 45.8% of the theory
HPLC: retention time: 2.3 min, LiChrosper 100 RP-18 (125-4), λ 220 nm, flow rate 0.5 ml/min, isocratic 50% acetonitile in $H_2O$ (0.1% TFA) retention time: 19.3 min, Nucleosil 7 $C_8$, λ=220 nm, flow rate 8 ml/min, isocratic 50% acetonitrile in $H_2O$ (0.1% TFA)
$^1H$ NMR (DMSO-$d_6$) $δ_H$: 0.8–1.0 (6 H, m, $H_{12}$ and $H_{13}$), 1.8–2.1 (3 H, m, $H_{11}$ and $H_{16}$), 2.2–2.4 (2 H, m, $H_{17}$), 3.4–3.7 (2 H, m, $H_{15}$), 3.7–4.1 (2 H, m, $H_{20}$ and $H_{21}$), 4.3–4.5 (1 H, dd, 5 Hz, 8 Hz, $H_9$), 4.8–5.1 (2 H, m, $H_2$), 5.8–6.2 (3 H, m, $H_{14}$, $H_{19}$), 7.2–7.5. (5 H, m, $H_2$—$H_6$), 8.2–8.3 (2 H, m, $H_{22}$ and $H_{23}$), 8.6–8.7 (1 H, m, $H_{24}$), 8.8–9.0 (1 H, d, 6 Hz, NH)
$^{13}C$ NMR (DMSO-$d_6$) $δ_C$: 136.8 ($C_1$), 127.9 ($C_2$, $C_3$), 127.8 ($C_4$, $C_5$), 128.4 ($C_6$), 66.7 ($C_7$), 156.3 ($C_8$), 57.9 ($C_9$), 170.8 ($C_{10}$), 29.7 ($C_{11}$), 18.5 ($C_{12}$, $C_{13}$), 63.7 ($C_{14}$), 47.2 ($C_{15}$), 25.1 ($C_{16}$), 27.9 ($C_{17}$), 200.3 ($C_{18}$), 71.1 ($C_{19}$), 146.1 ($C_{20}$, $C_{21}$), 128.3 ($C_{22}$, $C_{23}$), 146.4 ($C_{24}$)
MALDI-TOF-MS m/z: 424.6 Da (M+$H^+$, without chloride anion)

b) H-Val-Pro-$CH_2$—($N^+C_5H_5$)/$Cl^-$
Structural formula:

Preparation: The Z-protecting group is removed from Z-Val-Pro-$CH_2$—($N^+C_5H_4$)/$Cl^-$ by means of HBr/glacial acetic acid in a reaction time of 5 minutes. 2 ml of HBr/glacialacetic acid (33%) are added to 1.0 mmol of Z-protected peptide and the mixture is stirred at 23° C. for approx. 10 min. Concentration in vacuo is then carried out. The peptide is precipitated in the form of the hydrobromide from methanol by means of diethyl ether, suction-filtered and dried in vacuo. Empirical formula: $C_{16}H_{24}N_3O_2Cl$
Molecular weight: 325.84 Da
Yield: 97.7% of the theory
HPLC: retention time: 7.4 min, LiChrosper 100 RP-18 (125-4), λ=220 nm, flow rate 0.5 ml/min, isocratic 50% acetonitrile in H20 (0.1% TFA)
MALDI-TOF-MS m/z: 291.2 Da (M+$H^+$, without chloride anion)

1.2 Synthesis of H-Phe-Pro-$CH_2$—($N^+C_5H_5$)/$Cl^-$ a) Z-Phe-Pro-$CH_2$—($N^+C_5H_5$)/$Cl^-$
Structural formula:

Preparation: 2 ml of pyridine are added to 10 mmol of Z-Phe-Pro-chloromethyl ketone. The mixture is stirred at 23° C. for 4 days. The excess pyridine is distilled off at 2 mbar vacuum. The crude product is purified over 60 g of silica gel. In the chloroform/methanol eluate(9:1 parts by volume) initially the product is collected and, as the polarity of the eluant increases, the chloromethyl ketone is collected. Z-Phe-pro-pyridinium methyl ketone is finally subjected to HPLC purification. Empirical formula: $C_{28}H_{30}N_3O_4Cl$
Molecular weight: 508.01 Da
Yield: 69.6% of the theory
HPLC: retention time: 17 min, LiChrosorb RP-8 (Hibar), λ=220 nm, flow rate 8.0 ml/min, isocratic 50% acetonitrile in $H_2O$ (0.1% TFA) retention time: 3.4 min, LiChrosper RP-8 (125*4), λ=220 nm, flow rate 1.5 ml/min, gradient 30–80% acetonitrile in $H_2O$ (0.1% TFA) in 25 min retention time: 10.2 min, Nucleosil 7 $C_8$, λ=220 nm, flow rate 8 ml/min, isocratic 50% acetonitrile in $H_2O$ (0.1% TFA)
$^1H$ NMR (DMSO-$d_6$) δH: 1.7–2.1 (4 H, m, $H_{20}$, $H_{21}$), 2.7–3.0 (2 H, m, $H_{11}$), 3.4–3.9 (2 H, m, $H_{19}$), 4.4–4.6 (1 H, m, $H_9$), 4.6–4.8 (2 H, m, $H_{24}$, $H_{25}$), 5.0–5.1 (2 H, dd, $H_7$), 5.7–5.8 (1 H, d, $H_{18}$), 5.9–6.1 (2 H, dd, $H_{23}$), 7.2–7.4 (10 H, m, $H_2$—$H_6$, $H_{13}$—$H_{17}$), 8.6–8.8 (1 H, dd, $H_{28}$), 8.2–8.3 (2 H, d, $H_{26}$ and $H_{27}$), 8.8–8.9 (1 H, d, NH)
$^{13}C$ NMR (DMSO-$d_6$) $δ_C$: 136.8 ($C_1$), 127.9 ($C_2$, $C_3$), 127.6 ($C_4$, $C_5$), 128.4 ($C_6$), 65.5 ($C_7$), 156.3 ($C_8$), 54.1 ($C_9$), 170.9 ($C_{10}$), 36.4 ($C_{11}$), 137.6 ($C_{12}$), 126.6 ($C_{13}$, $C_{14}$), 128.4 ($C_{15}$, $C_{16}$), 129.3 ($C_{17}$), 63.1 ($C_{18}$), 46.9 ($C_{19}$), 25.1 ($C_{20}$), 27.6 ($C_{21}$), 200.7 ($C_{22}$), 66.3 ($C_{23}$), 146.2 ($C_{24}$, $C_{25}$), 128.2 ($C_{26}$, $C_{27}$), 146.4 ($C_{28}$)MALDI-TOF-MS m/z: 472.8 Da (M+$H^+$, without chloride anion)

(b) H-Phe-Pro-$CH_2$—($N^+C_5H_5$)/$Cl^-$
Structural formula:

Preparation: The Z-protecting group is removed from Z-Phe-Pro-$CH_2$-($N^+C_5H_4$)/$Cl^-$ after a reaction time of 5 minutes. 2 ml of HBr/glacial acetic acid (33%) are added to 1.0 mmol of Z-protected peptide and the mixture is stirred at 23° C. for approx. 10 minutes. Concentration in vacuo is then carried out. The peptide is precipitated in the form of the hydrobromide using diethyl ether, suction-filtered and dried in vacuo.
Empirical formula: $C_{20}H_{24}N_3O_2Cl$
Molecular weight: 373.88 Da
Yield: 98% of the theory
HPLC: retention time: 6.9 min, LiChrosper 100 RP-18 (125-4), λ=220 nm, flow rate 0.5 ml/min, isocratic 50% acetonitrile in $H_2O$ (0.1% TFA)
MALDI-TOF-MS m/z: 337.2 Da (M+$H^+$, without chloride anion)

1.3 Synthesis of H-Gly-Pro-Val-Pro-$CH_2$—($N^+C_5H_5$)/$Cl^-$ a) Z-Gly-Pro-Val-Pro-$CH_2$—($N^+C_5H_5$)/$Cl^-$

Structural formula:

Preparation: 2 ml of pyridine are added to 10 mmol of Z-Gly-Pro-Val- Pro-chloromethylketone. The mixture is stirred at 23° C. for 4 days. The excess pyridine is distilled off at 2 mbar vacuum. Z-Gly-Pro-Val-pro-pyridinium methyl ketone is subjected to HPLC purification. Empirical formula: $C_{31}H_{40}N_5O_6Cl$
Molecular weight: 614.14 Da
HPLC: retention time: 17.4 min, LiChrosorb RP 8 Hibar, λ=220 nm, flow rate 8 ml/min, isocratic 50% acetonitrile in $H_2O$ (0.1% TFA) retention time: 5.4 min, LiChroCART 100 RP-18 (250-4), λ=220 nm, flow rate 0.5 ml/min, isocratic 50% acetonitrile in $H_2O$ (0.1% TFA) retention time: 17.7 min, Nucleosil 100 7 $C_8$, λ=220 nm, flow rate 5 ml/min, isocratic 50% acetonitrile in $H_2O$ (0.1% TFA)
$^{13}C$ NMR (DMSO-$d_6$) $δ_C$: 134.4 ($C_1$), 128.9 ($C_2$, $C_3$), 128.2 ($C_4$, $C_5$), 129.8 ($C_6$), 65.3 ($C_7$), 157.2 ($C_8$), 39.0 ($C_9$), 165.7 ($C_{10}$), 56.0 ($C_{11}$), 41.6 ($C_{12}$), 24.6 ($C_{13}$), 29.0 ($C_{14}$), 170.5 ($C_{15}$), 52.1 ($C_{16}$), 171.9 ($C_{17}$), 30.3 ($C_{18}$), 18.6, 19.3 ($C_{19}$, $C_{20}$), 58.9 ($C_{21}$), 47.2 ($C_{22}$), 25.0 ($C_{23}$), 29.4 ($C_{24}$), 196.5 ($C_{25}$), 65.8 ($C_{26}$), 137.9 ($C_{27}$, $C_{28}$), 129.1 ($C_{29}$, $C_{30}$), 146.5 ($C_{31}$)
MALDI-TOF-MS m/z: 579.7 Da (M+H$^+$, without chloride anion)

b) H-Gly-Pro-Val-Pro-CH$_2$—(N$^+$C$_5$H$_5$)/Cl$^-$
Structural formula:

Preparation: The Z-protecting group is removed from Z-Phe-Pro-CH$_2$—(N+C$_5$H$_4$)/Cl$^-$ after a reaction time of 5 minutes. 2 ml of HBr/glacial acetic acid (33%) are added to 1.0 mmol of Z-protected peptide and the mixture is stirred at 23° C. for approximately 10 minutes. Concentration invacuo is then carried out. The peptide is precipitated in the form of the hydrobromide using diethyl ether, suction-filtered and dried in vacuo. Empirical formula: $C_{23}H_{34}N_5O_4Cl$
Molecular weight: 480.0 Da
Yield: 95% of the theory
MALDI-TOF-MS m/z: 443.9 Da (M+H$^+$, without chloride anion)

BREAKDOWN OF UNSTABLE DP IV-INHIBITORS AND OF THEIR MASKED FORMS IN AQUEOUS SOLUTION

Figure 1:
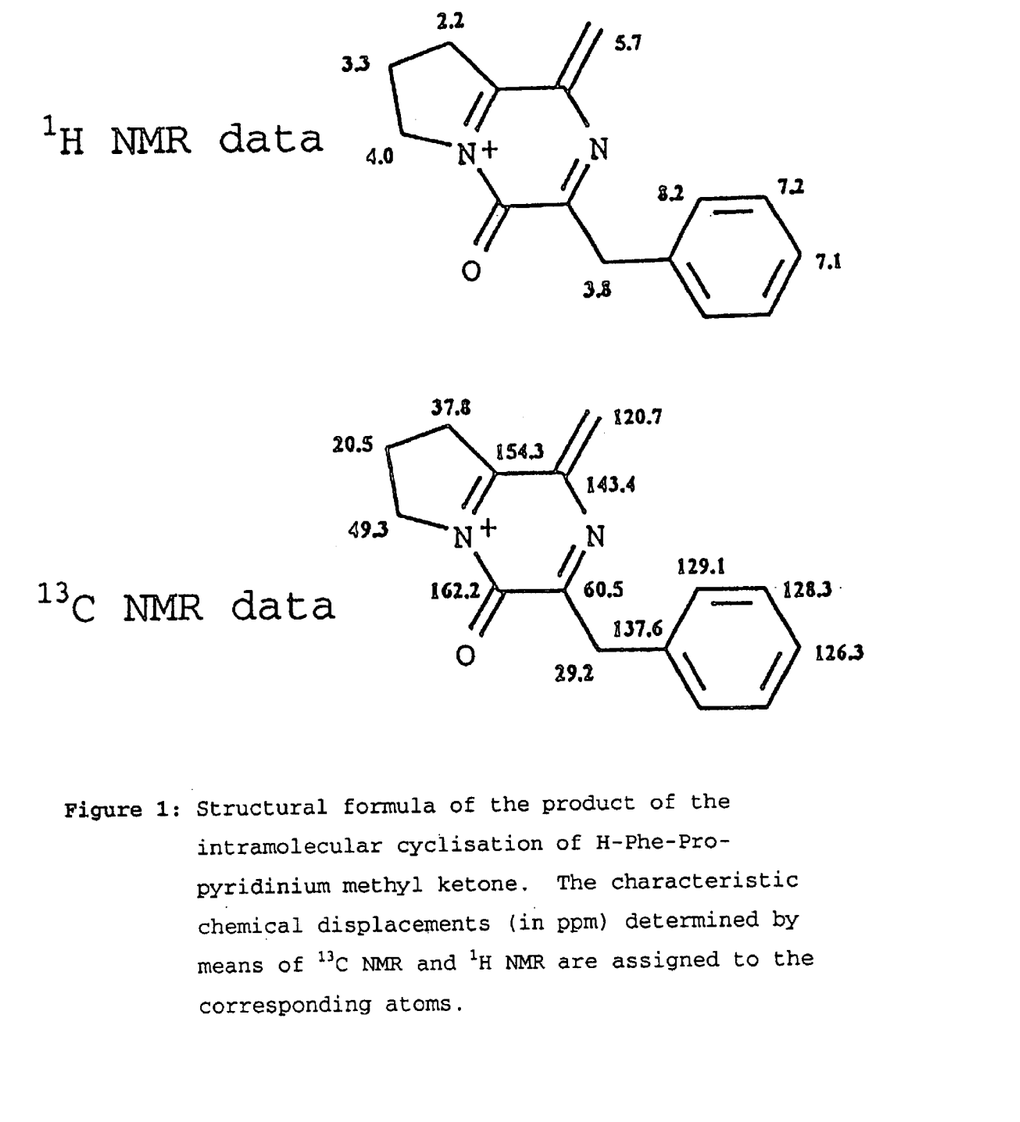
FIG. 1 shows Structural formula of the product of the intramolecular cyclisation of H-Phe-Pro-pyridinium methyl ketone. The characteristic chemical displacements (in ppm) determined by means of $^{13}C$ NMR and $^1H$ NMR are assigned to the corresponding atoms.
Figure 2:
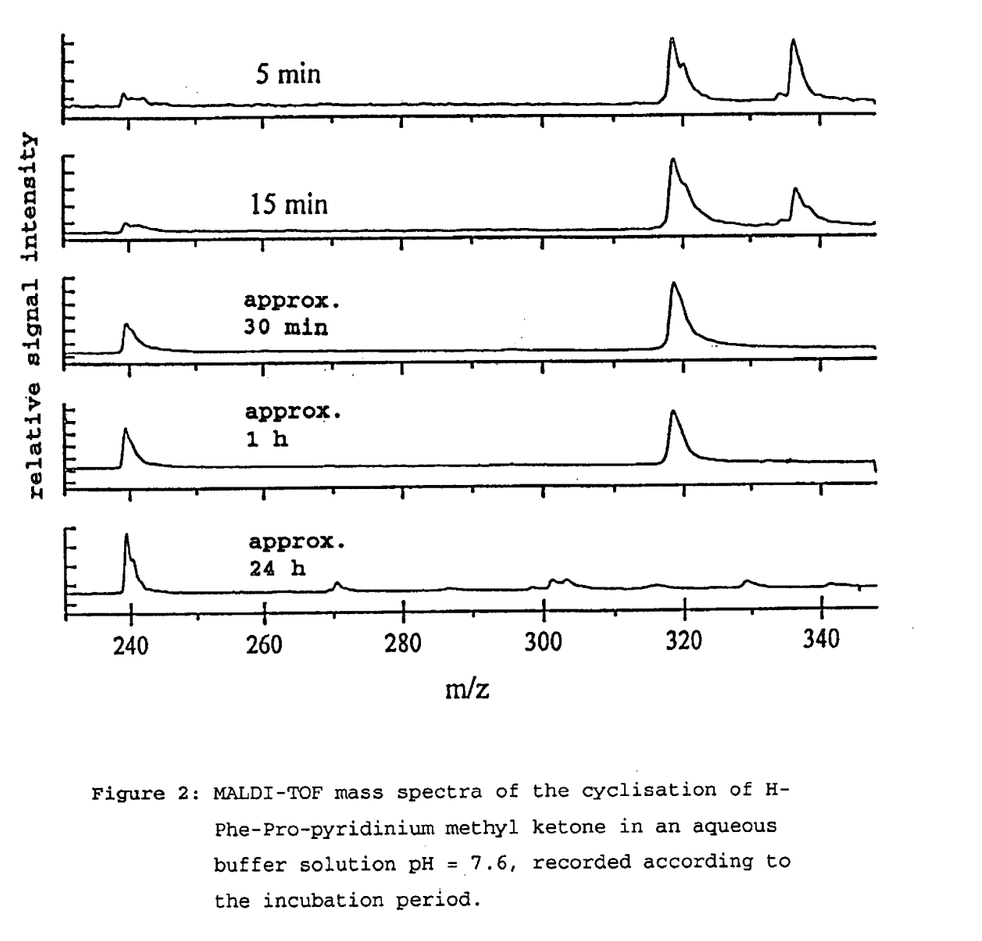
FIG. 2 shows a MALDI-TOF mass spectra of the cyclisation of H-Phe-Pro-pyridiniummethyl ketone in an aqueous buffer solution pH=7.6, recorded according to the incubation period.
Figure 3:
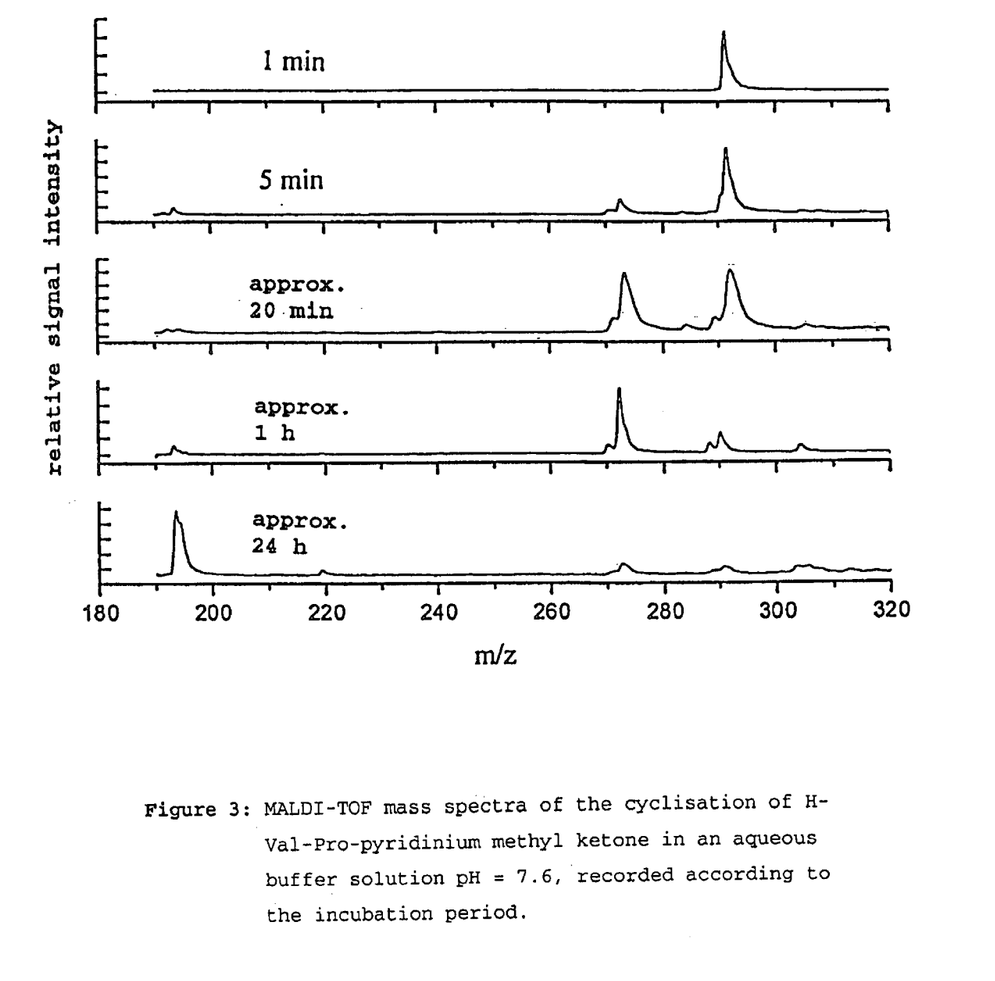
FIG. 3 shows a MALDI-TOF mass spectra of the cyclisation of H-Val-Pro-pyridinium methyl ketone in an aqueous buffer solution pH=7.6, recorded according to the incubation period

To analyze the stability of the inhibitors prepared under 1.1 and 1.2, the inhibitors were incubated in an aqueous buffer solution and their intramolecular cyclisation reaction was monitored by means of MALDI-TOF mass spectrometry (FIGS. 2 and 3). The products of that reaction are the respective pyrazine derivatives (FIG. 1).

The breakdown of H-Phe-Pro-pyridinium metyl ketone having the molecular weight of 337.2 Da to the cyclic pyrazine derivative having the molecular weight of 319.2 Da, with removal of water, is completed quantitatively within a period of 30 minutes (FIG. 2).

The breakdown of H-Val-Pro-pyridiniummethyl ketone having the molecular weight of 291.2 Da to the cyclic pyrazine derivative having the molecular weight of 273.2 Da, with removal of water, is completed quantitatively within a period of 60 minutes (FIG. 3).

Figure 4:
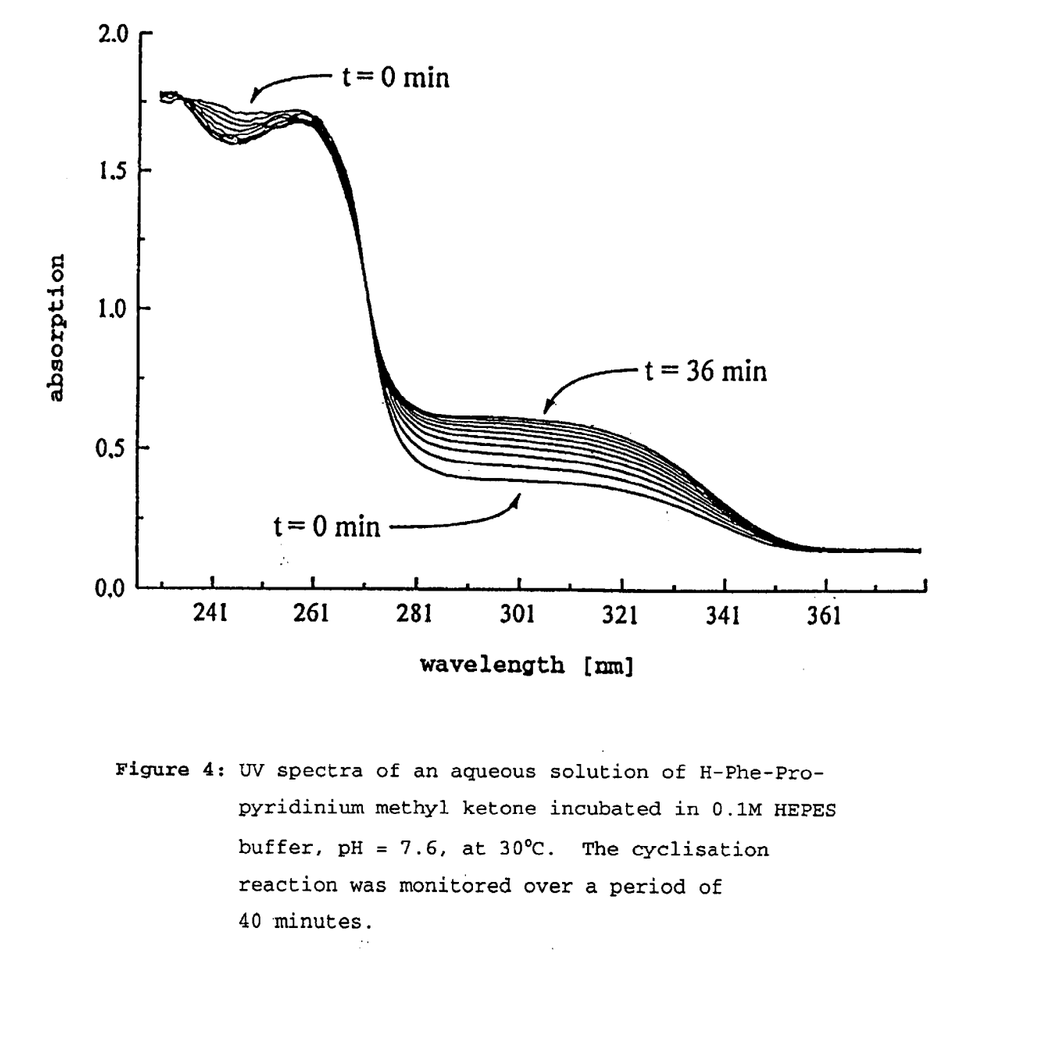
FIG. 4 shows UV spectra of an aqueous solution of H-Phe-Pro- pyridinium methyl ketone incubated in 0.1 M HEPES buffer, pH=7.6, at 30° C. The cyclisation reaction was monitored over a period of 40 minutes.

The formation of the double bond system of the pyrazine, which takes place during the intramolecular reaction, enables quantitative analysis of the cyclisation process by means of UV spectrometry (FIG. 4). The rate constants determined there from for the intramolecular cyclisation of unstable DP IV-inhibitors in 0.1 M HEPES buffer, pH=7.6, 25° C., are shown in Table 1.

TABLE 1

PARAMETERS OF THE CYCLISATION OF UNSTABLE DP IV-INHIBITORS

| Compound | k min$^{-1}$ | Half life (min) |
|---|---|---|
| H-Val-Pro-CH$_2$-(N$^+$C$_5$H$_5$) | 8.7 × 10$^{-4}$ (± 4 × 10$^{-5}$) | 13.3 |
| H-Phe-Pro-CH$_2$-(N$^+$C$_5$H$_5$) | 1.2 × 10$^{-3}$ (± 3.9 × 10$^{-5}$) | 9.6 |

In contrast thereto, the compound H-Val-Pro-CH$_2$—(N$^+$C$_5$H$_5$) in the form of H-Gly-Pro-Val-Pro-CH$_2$—(N+C$_5$H$_5$) according to the invention has proved to be completely stable over a period of 24 hours under identical conditions.

INTERACTION OF UNSTABLE DP IV-INHIBITORS OR COMPOUNDS COMPRISING DIPEPTIDYL PEPTIDASE IV ACCORDING TO THE INVENTION IN AQUEOUS SOLUTION

Figure 5:
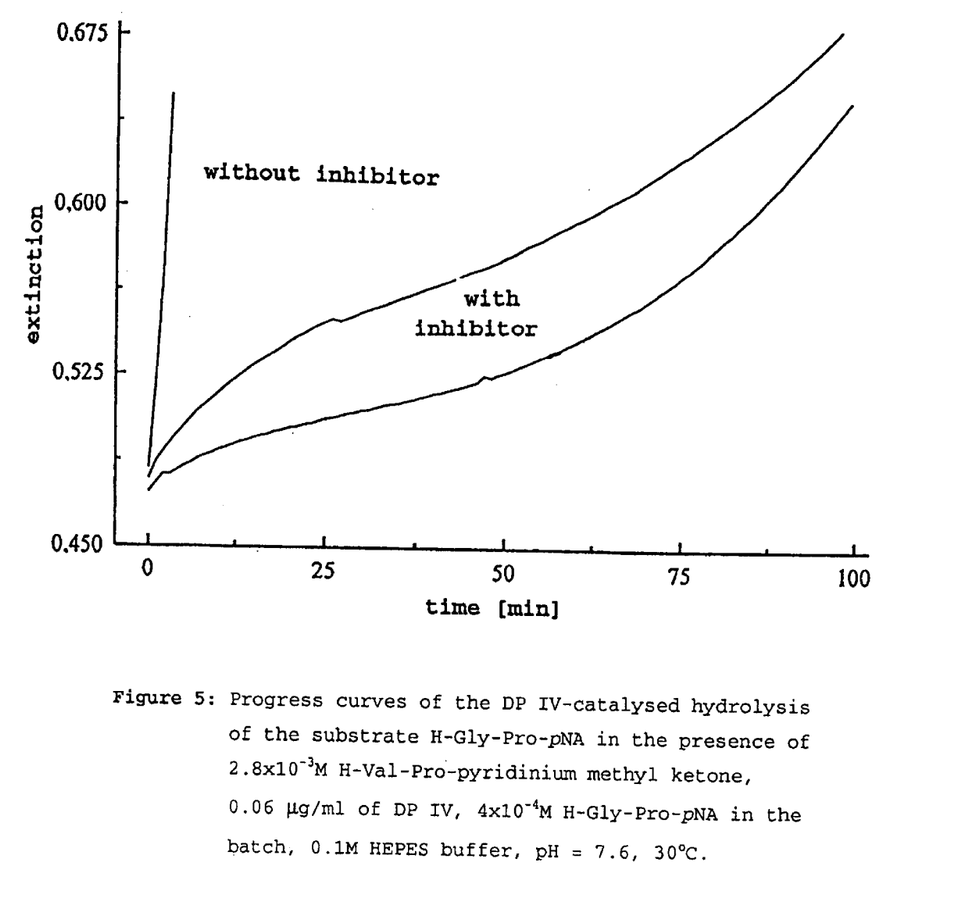
FIG. 5 shows a Progress curves of the DP IV-catalysed hydrolysis of the substrate H-Gly-Pro-pNA in the presence of 2.8×10–3 M H-Val-Pro-pyridiniummethyl ketone, 0.06 µg/ml of DP IV, 4×10–4 M H-Gly-Pro-pNA in the batch, 0.1 M HEPES buffer, pH=7.6, 30° C.
Figure 6:
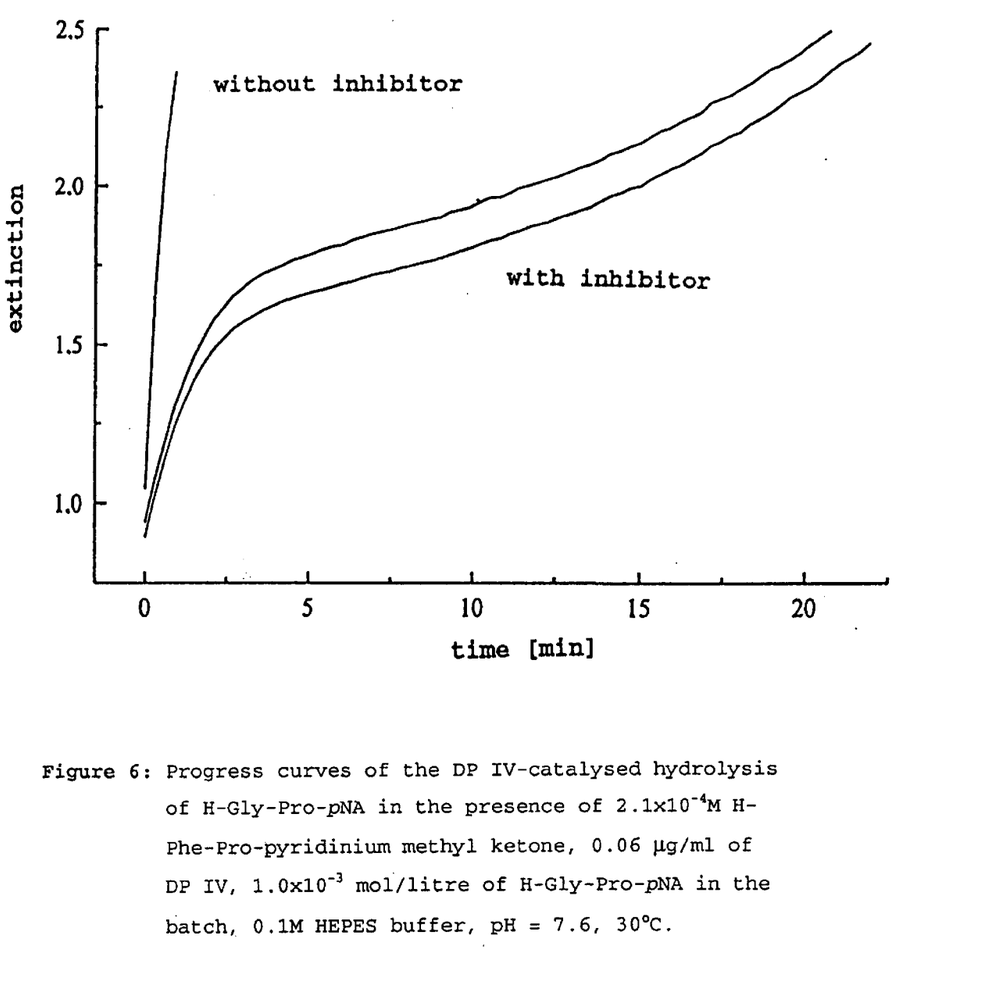
FIG. 6 shows a Progress curves of the DP IV-catalysed hydrolysis of H-Gly-Pro-pNA in the presence of $2.1 \times 10^{-4}$M H-Phe-Pro-pyridinium methyl ketone, 0.06 µg/ml of DP IV, $1.0 \times 10^{-3}$ mol/litre of H-Gly-Pro-pNA in the batch, 0.1 M HEPES buffer, pH=7.6, 30° C.

When the DP IV target enzyme is incubated with unstable inhibitors in the presence of a substrate, inhibition of the enzyme is observed initially; the inhibition subsides again as the experimental time progresses as a result of the intramolecular cyclisation of the inhibitor which takes place in parallel, since the concentration of the inhibitor in the reaction solution decreases as a result of the spontaneously occurring chemical reaction. That effect is shown in FIGS. 5 and 6. Because of the time-dependent drop in the concentration of the inhibitor, the rate of the enzyme-catalysed hydrolysis of the substrate increases again as time progresses.

Figure 7:
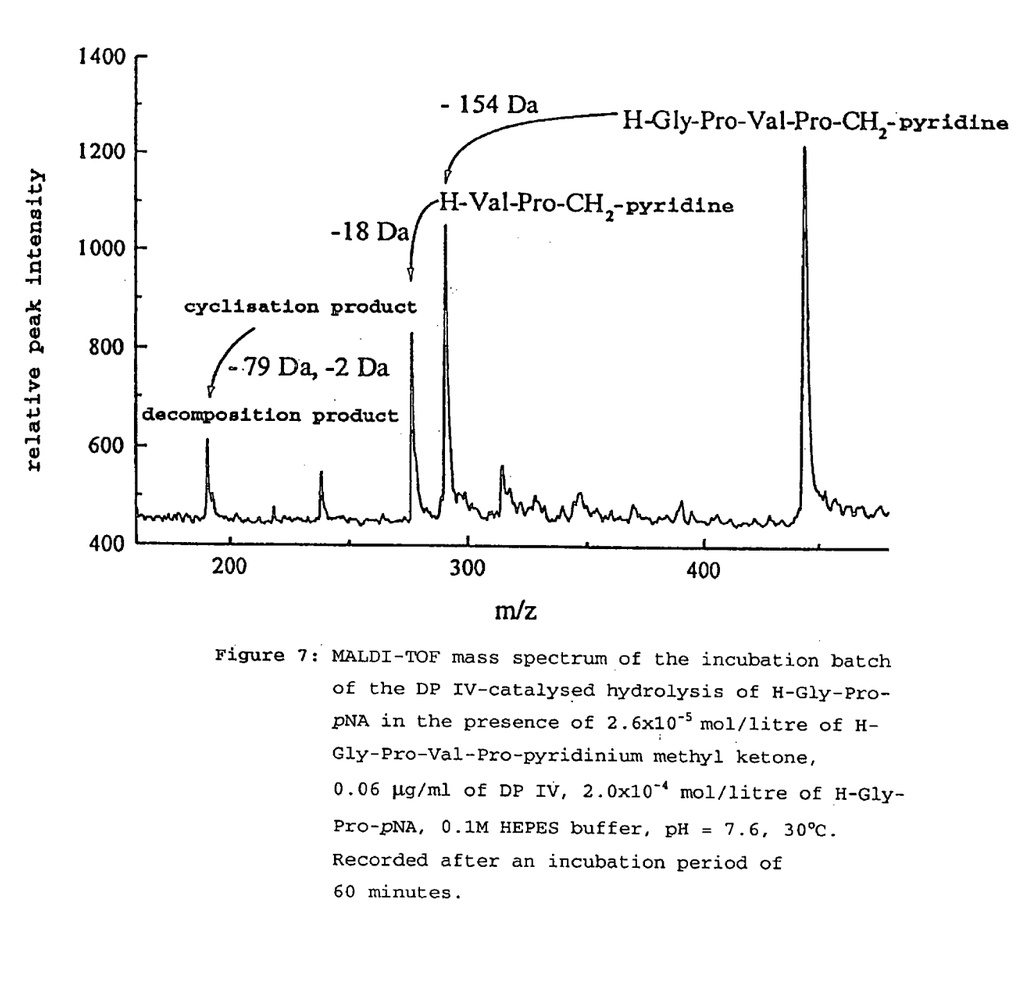
FIG. 7 shows a MALDI-TOF mass spectrum of the incubation batch of the DP IV-catalysed hydrolysis of H-Gly-Pro-pNA in the presence of $2.6 \times 10^{-5}$ mol/litre of H-Gly-Pro-Val-Pro-pyridinium methyl ketone, 0.06 µg/ml of DP IV, $2.0 \times 10^{-4}$ mol/litre of H-Gly-Pro-pNA, 0.1 M HEPES buffer, pH=7.6, 30° C. Recorded after an incubation period of 60 minutes.
Figure 8:
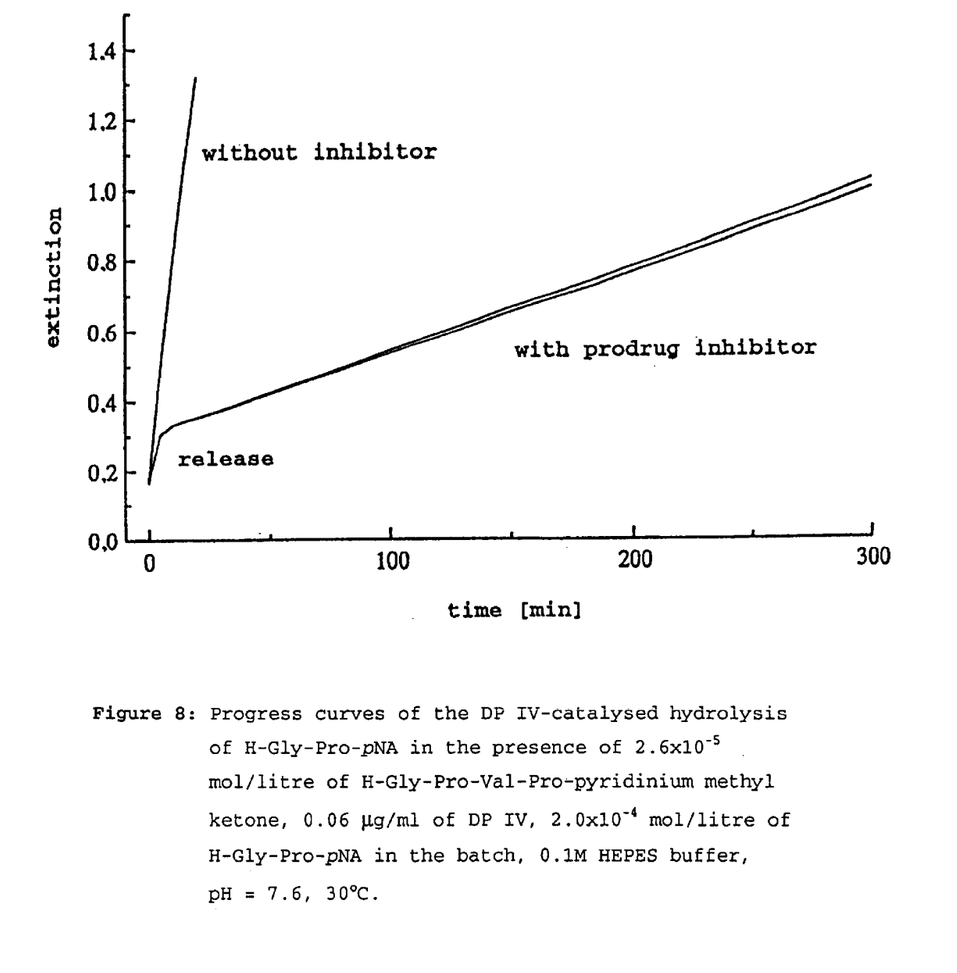
FIG. 8 shows Progress curves of the DP IV-catalysed hydrolysis of H-Gly-Pro-pNA in the presence of $2.6 \times 10^{-5}$ mol/litre of H-Gly-Pro-Val-Pro-pyridiniummethyl ketone, 0.06 µg/ml of DP IV, $2.0 \times 10^{-4}$ mol/litre of H-Gly-Pro-pNA in the batch, 0.1 M HEPES buffer, pH=7.6, 30° C.

In contrast to the non-masked DP IV-inhibitors, the compound H-Gly-Pro-Val-Pro-Ch$_2$—(N$^+$C$_5$H$_5$) according to the invention has proved to be stable over a period of 24 hours in buffered aqueous solution in the absence of an enzyme. The active DP IV-inhibitor H-Val-Pro-CH$_2$—(N$^+$C$_5$H$_5$) is released only as a result of the addition of the DP IV enzyme (used here by way of example also to release the DP IV-inhibitor) with removal of the N-terminal dipeptide H-Gly-Pro-OH. Accordingly, in the mass spectrum (FIG. 7) markedly more than 50% of the incubated compound according to the invention can be detected even after an incubation period of 60 minutes. Owing to that delayed release, surprisingly there is also observed, in addition to the desired effective inhibition of the target enzyme, a markedly prolonged activity combined with markedly reduced concentration of the compound according to the invention compared with the unstable DP IV-inhibitors as shown in FIG. 8.

What is claimed is:

1. Compounds of inhibitors of the enzymatic activity of dipeptidyl peptidase IV (DP IV), which compounds have the general formula A—B—C, wherein A is an amino acid, B is a chemical bond between A and C or is an amino acid, and C is an inhibitor of DP IV wherein said inhibitor is a dipeptide compound having an active carbonyl group at the C-terminus wherein said inhibitor does not contain a di- or tri-fluoroalkyl ketone group.

2. Compounds according to claim 1, wherein B is selected from the group consisting of proline, hydroxyproline, thiazolidinecarboxylic acid, dehydroproline, pipecolic acid, 2-azetidinecarboxylic acid, 3-azetidinecarboxylic acid and 2-aziridinecarboxylic acid.

3. Compounds according to claim 1 wherein, B is proline or hydroxyproline.

4. Compounds according to claim 1 wherein said dipeptide compound is selected from the group consisting of Ile-Thiazolidine, Ile-Pyrrolidine, Val-Thiazolidine and Val-Pyrrolidine.

5. Compounds according to claim 1 wherein said inhibitors are present in salt form.

6. Compounds according to claim 1 wherein said inhibitors are present as organic salts such as acetates, succinates, tartrates or furnarates or inorganic acid radicals such as phosphates or sulphates.

7. Compounds according to claim 1 wherein A—B is a dipeptide of formula Ile-Pro or Gly-Pro and C is a dipeptidyl alkyl ketone compound.

8. A pharmaceutical composition for oral administration comprising the compound of claim 1 and customary pharmaceutical carriers or excipients.

9. A compound of claim 1 wherein C is an inhibitor of DP IV selected from a group consisting of; a dipeptidyl chloroalkyl ketone, a dipeptidyl pyridinium methyl ketone and a dipeptidyl alkyl ketone compound exempting di- and tri-fluoroalkyl ketone compounds.

10. Compounds of inhibitors of the enzymatic activity of dipeptidyl peptidase IV (DP IV), which compounds have the general formula A—B—C, wherein A is an Amino Acid B is a chemical bond between A and C or is an amino acid, and C is an inhibitor of DP IV wherein said inhibitor is a dipeptidyl cyanide.

11. Compunds accoding to claim 10, wherein B is selected from the group consisting of proline, hydroxyproline, thiazolidinecarboxylic acid, dehydroproline, pipecolic acid, 2-azetidinecarboxylic acid, 3-azetidinecarboxylic acid and 2-azirdinecarboxylic acid.

12. Compounds according to claim 10 wherein, B is proline or hydroxyproline.

13. Compounds according to claim 10 wherein said dipeptide is selected from the group consisting of Ile-Thiazolidine, Ile-Pyrrolidine, Val-Thiazolidine and Val-Pyrrolidine.

14. Compounds according to claim 10 wherein said inhibitors are present in salt form.

15. Compounds according to claim 10 wherein said inhibitors are present as organic salts such as acetates, succinates, tartrates or fumarates or inorganic acid radicals such as phosphates or sulphates.

16. A pharmaceutical composition for oral administration comprising the compound of claim 10 and customary pharmaceutical carriers or excipients.

* * * * *